(12) United States Patent
Beck et al.

(10) Patent No.: US 6,807,876 B2
(45) Date of Patent: Oct. 26, 2004

(54) TESTING OR SETTING DEVICE FOR A PDD OR PDT SYSTEM, OR FOR TRAINING ON SUCH A SYSTEM AND TISSUE PHANTOM

(75) Inventors: Gerd Beck, Tuttlingen (DE); André Erhardt, Wurmlingen (DE); Klaus M. Irion, Liptingen (DE)

(73) Assignee: Karl Storz GmbH & Co. KG (DE)

( * ) Notice: Subject to any disclaimer, the term of this patent is extended or adjusted under 35 U.S.C. 154(b) by 376 days.

(21) Appl. No.: 09/872,940

(22) Filed: Jun. 1, 2001

(65) Prior Publication Data

US 2002/0077677 A1 Jun. 20, 2002

Related U.S. Application Data

(63) Continuation of application No. PCT/EP99/09507, filed on Dec. 6, 1999.

(51) Int. Cl.[7] .............................................. G01N 19/00
(52) U.S. Cl. ....................................................... 73/865.9
(58) Field of Search ................................ 73/1.01, 865.9; 356/243.1, 243.5, 243.6, 243.8; 600/175, 160

(56) References Cited

U.S. PATENT DOCUMENTS 6,361,490 B1 * 3/2002 Irion et al. .................. 600/175

FOREIGN PATENT DOCUMENTS

| EP | 0 368 436 | 5/1990 |
|---|---|---|
| WO | WO98/11945 | 3/1998 |

OTHER PUBLICATIONS

J. Linford et al, Development of a Tissue–Equivalent Phantom for Diaphanography, Med. Phys. 13(6), Nov.Dec. 1986, pp. 869–875.

J.B. Guidt et al, Standard Media for Particle Size and Number–Density Calibrations in Single, Multiple and Dependent Scattering, Part. Syst. Charact. 7, 1990, pp. 36–43.

H.J. van Staveren et al, Light Scattering in Intralipid–10% in the Wavelength Range of 400–1100 NM, Applied Optics, Nov. 1991, pp. 4507–4514.

A.J. Durkin et al, Optically Dilute, Absorbing, and Turbid Phantoms for Fluorescence Spectroscopy of Homogeneous and Inhomogeneous Samples, Applied Spectroscopy, vol. 47, No. 12, pp. 2114–2121.

M. Firbank et al, A Design for a Stable and Reproducible Phantom for Use in Infra–Red Imaging and Spectroscopy, Phys. Med. Biol. 38, 1993, pp. 847–853.

(List continued on next page.)

*Primary Examiner*—Robert Raevis
(74) *Attorney, Agent, or Firm*—St. Onge Steward Johnston & Reens LLC

(57) ABSTRACT

A testing or setting device for a PDD or PDT system or for training on such a system, which includes a lighting system, is provided with a housing in which the PDD or PDT system can be at least partially accommodated. The device is characterized in that a tissue phantom is installed in the housing in such a way that the surface of the tissue phantom can be at least partially lit by the lighting system and observed by the observation system, and that the tissue phantom includes at least one luminescent area. A tissue phantom, appropriate for use in the invention's device, has at least one luminescent area and is characterized by the fact that it has at least one additional area, whose luminescent characteristics differ from those of the first luminescent area.

19 Claims, 2 Drawing Sheets

OTHER PUBLICATIONS

U. Sukowski et al, Preparation of Solid Phantoms with Defined Scattering and Absorption Phoperties for Optical Tomography, Phys. Med. Biol. 41, 1996, pp. 1823.

G.C. Beck et al, Design and Characterisation of a Tissue Phantom System for Optical Diagnostics, Lasers Med. Sci. 1998, pp. 160–171.

R. Bays et al, A Three–Dimensional Optical Phantom and its application in Photodynamic Therapy, Swiss Federal Institute of Technology, 26 pgs.

G. Wagnieres et al, Design and Chracterisation of a Phantom Which Simultaneously Simulates Tissue Optical Properties Between 400 and 650 NM, Proc. SPIE 2926, 10 pgs.

G.C. Beck, Developing Optimized Tissue Phantom Systems for Optical Biopsies, Institut fur Lasertechnologien, 10 pgs.

G.C. Beck, Gewebephantomsystem Und Tiefenauflosender Fluoreszenznachweis Fur Die Optishche Diagnostik In Der Medizin, Institut fur Lasertechnologien, 1998, 80 pgs.

* cited by examiner

TESTING OR SETTING DEVICE FOR A PDD OR PDT SYSTEM, OR FOR TRAINING ON SUCH A SYSTEM AND TISSUE PHANTOM

CROSS-REFERENCE TO RELATED APPLICATIONS

This application is a continuation of pending International Application PCT/EP99109507 filed on Dec. 6, 1999, which designates the United States. This application claims priority of German Patent Application DE19855853.8 filed on Dec. 4, 1998.

FIELD OF THE INVENTION

The invention relates to a testing or setting device for a PDD or PDT system or for training on such a system, as well as to a process for testing or setting a PDD or PDT system and to a tissue phantom and a process for producing a tissue phantom.

BACKGROUND OF THE INVENTION

Photo-dynamic diagnosis (PDD) or therapy (PDT) systems are widely used in medical practice to detect and/or to treat malignant as well as benign tissue degenerations. These practices make use of photo-sensitizers, which accumulate specifically in the tissue to be examined and luminesce with light stimulants (photo-dynamic diagnosis) or alternatively at high photo-sensitizer doses and high illuminating strength they lead to a photo-toxic effect, through which the diseased tissue is destroyed (photo-dynamic therapy). In particular, for photo-dynamic diagnosis, luminescent substances occurring in the body can be brought into play. A combined fluorescence/auto-florescence PDD system is described in the publication Endo World THOR No. 27-E, 1999, by the Karl Storz GmbH & Co. KG.

PDD and PDT systems include a lighting system, whose light serves to stimulate luminescence, that is, fluorescence or phosphofluorescence substance for instance. In addition, PDD systems as well as many PDT systems are provided with an observation system, with which the tissue area to be examined or treated can be observed, or it is also possible to conduct only an intensity measurement of the luminescent light. Since the luminescence tends to be considerably weaker than the reflection of the light stimulant, a filter system is usually provided to permit observation of the luminescent effect. If the process takes advantage of the fact that the luminescent light has different wavelengths from the stimulant light, then a wavelength-selective filter system is used. On the other hand, if the process with pulsed stimulant light employs a luminescent light emission that is delayed with respect to the reflection, then a time-selective filter system is used. The filter system, which also includes the radiation or time sensitivity of the detector system, can be designed in such a way that reflected light can also be used to observe the relevant tissue area, as is described for instance in WO 97/11636 and in WO 98/43534; the lighting unit can also provide for an additional broadband illumination.

PDD and PDT systems include components that can age or become damaged, such as lamps, light cables, filters, or lens systems, as well as components that require initial or repeated setting or adjustment, such as the light source or the camera, for which the brightness or color balance may have to be adjusted. The optimal setting in each case can also depend on the particular application or on the user. If this testing or setting is not carried out until the system is actually in use, this can unwittingly place a burden on the patient. The same is true for the training of the user that may be required because of the complexity of such systems and their specific application.

It is advisable therefore for a PDD or PDT system to be tested and, if necessary, adjusted prior to use, with the help of a device. Such a device, which can also be used for training, as well as a related process, is known from WO 98/11945. That invention provides for a target that reflects the illuminating light of the PDD or PDT system, and includes a light source that emits light in the wavelength range of the fluorescent spectrum of the particular photo-sensitizer. In order to test or set a PDD or PDT system, it is placed in the device, the illumination intensity of the light stimulant is received by a photo element, and a control unit controls the light source according to a predetermined function in order to duplicate the luminescent effect.

This device is costly because of the need for a light source and a control unit, and the reproduction of the luminescent effect can have only a limited fidelity.

One task of the present invention is to provide a device for testing and/or setting a PDD or PDT system or for training on such a system, a device which is as simple in construction as possible, is easy to handle, and allows for the most realistic possible imitation of the luminescent effect, as well as a related process for testing and/or setting a PDD or PDT system.

The invention fulfills this task through the characteristics of claims 1 and 13. A tissue phantom, which has at least one luminescent area, is arranged in a housing in which the PDD or PDT system can be at least partially accommodated, in such a way that it can be at least partially illuminated by the lighting system of the PDD or PDT system. As a result, a realistic depiction of the luminescent effect becomes possible without the need for additional devices for producing the luminescent light.

In an advantageous application of the invention, the housing includes a hollow space in which the PDD or PDT system for testing, setting, or training can be at least partially accommodated. The housing can be designed as described in U.S. Pat. No. 5,820,547. It is particularly advantageous, in this case, if the hollow space is closed off and if there is an aperture equipped with a preferably light-sealed closing to accommodate one part of the PDD or PDT system, to simulate the lighting conditions during an intervention inside the body. This is particularly advantageous when the PDD or PDT system includes an endoscope or an operating microscope, through which the illumination is directed to the tissue or through which the tissue can be observed. There can also be several apertures of various diameters for endoscopes of different diameters, or apertures arranged at an angle to one another for endoscopes with various viewing angles. In addition, other apertures or devices may be provided, through which surgical instruments can be introduced for instance, or through which independent lighting or observation is possible, or through which rinsing can take place since work is frequently carried out in practice in common salt solution.

To permit the use of the invention's device in a sterile area or with sterile implements or instruments, it is also advantageous if a sterile foil can be placed in the housing to protect the sterile part from contamination each time it is introduced. This foil can also encase the entire device, possibly along with additional substitute tissue phantoms, to permit unrestricted use in a sterile area. On the other hand, the device can be designed so that the PDD or PDT system can be accommodated in the housing with a sterile foil which protects the inserted sterile part from contamination. It is thereby possible to test the PDD or PDT system during an operation as well, without affecting its sterility. Of course the device can also be designed so as to be sterilizable as a whole; in this case the tissue phantom can be equipped with a hermetically sealed casing. The device or the tissue phantom itself can also be produced for one-time use.

In another advantageous application, the tissue phantom is secured on an adjustable, for instance sliding, mounting. This has the advantage that the tissue phantom can be moved into the focal area of the lighting or observation system and then out of it again, without the need to displace the PDD or PDT system itself. As a result, the conditions of actual use can be simulated in a simple manner.

In another advantageous application, the tissue phantom is replaceable. Thus, by exchanging the tissue phantom, it is possible to use the invention's device for various PDD or PDT systems, for various application cases, for instance for various tissue types or organs, or else with various photo-sensitizers or luminescence modes. Likewise it is possible, as a result, to replace a damaged, soiled, non-sterile tissue phantom, or one that has become unusable through fading of the photo-sensitizer.

In another advantageous application, several tissue phantoms are provided. This makes it possible, for instance, to observe simulations of different tissue types simultaneously or at brief intervals, or else to continue treating them immediately if a tissue phantom has become unusable as a result of fading.

In another advantageous application of the invention, the tissue phantom is executed in such a way as to copy the optical, thermal, electrical, or mechanical properties of a particular human or animal tissue or organ. This permits a realistic depiction of the tissue or organ even when the tissue phantom is touched, for instance by the PDD or PDT system, or reacts in some way other than merely through reflected or luminescent light. The properties of the tissue phantom can, in particular, be selected so that the tissue phantom behaves in similar way as a particular human or animal tissue when it is treated with medical instruments, for instance HF or resectioning instruments.

To achieve an especially realistic optical image, in another advantageous model, the part of the tissue phantom that is to be illuminated by the lighting system and to be observed by the observation system, if present, is copied from a tissue areas that is to be observed or treated, to match the radiation characteristics of the reflection and the luminescent properties. In particular, the radiation properties and/or the temporal behavior of the luminescent light, the intensity of the luminescence, and the spatial distribution of the luminescence are preferably copied from the corresponding properties of the tissue; in addition, absorption, reflection, and scattering can be copied from the corresponding tissue properties. For this purpose, it is not necessary to use the same substances, or even the same luminescent substances which cause the corresponding properties in vivo; instead, other substances with similar properties or admixtures of such substances can be used. It is also possible to simulate the simultaneous appearance of several luminescent modes. To copy the appearance of a surface tumor, a layer of the tissue phantom that duplicates the optical properties of the relevant tissue layer can be thickened by a factor of about three in the area in which luminescent substances are particularly concentrated.

Because the recognizability of tissue modification depends also on the geometric shape of the tissue area to be observed and/or treated, it is also advantageous if the part of the tissue phantom to be illuminated by the lighting system and observed by the observation system is shaped so that the upper surface of the corresponding tissue area is copied. It is particularly advantageous if the relevant part of the tissue phantom has a hollow spherical or tube-like shape, because frequent applications of PDD or PDT tend to involve hollow spherical or tube-like organs and because frequently the subject field curvature of the image-producing unit of the PDD or PDT system is also adjusted to the curvature of the relevant organ. By creating images of finer and finer structures, possibly including the microscopic roughness of the surface, a particularly good approximation of the appearance of the relevant natural tissue can be obtained.

Because it is not always possible to adjust the fluorescent emission spectrum of the tissue phantom exactly to the spectrum produced in vivo by the fluorescent substance introduced into the body tissue or present there, it is also possible to provide a filter system or an additional lighting system so that the emission spectrum of the tissue phantom is adjusted better to the emission spectrum of the bodily tissue in vivo. In particular, when two or more luminescent substances are contained in the tissue phantom, it can be advantageous to provide an additional filter which controls or corrects the relative intensity of the light stimulant for the various luminescent substances.

The invention's process for testing or setting a PDD or PDT system includes the following steps:

- the PDD or PDT system to be tested or set is placed at least partially in a housing or in the invention device;
- the lighting system of the PDD or PDT system is directed to the surface of the tissue phantom and this surface is illuminated;
- the illuminated surface of the tissue phantom is at least partially observed by the observation system;
- at least one measurement or observation result is recorded, which is a value for the luminescent intensity or for the detection capability or proper functioning of the PDD or PDT system; and
- if necessary, a corrective setting of the PDT or PDT system is made.

Through this process it is possible to test the functionality of a PDD or PDT system under realistic conditions without thereby disturbing the patient. Similarly, with no burden on the patient, it is possible to find the optimal setting for a particular application or a standard setting for light intensity, general sensitivity, or radiation sensitivity. In particular, the optical differentiation between luminescent effect and background light can also be set by this means, for instance to the subjectively strongest color contrast for a particular user, through adjustment of the DAC setting of the RGB camera in use, or it can also be adjusted automatically to a standard value.

Tissue phantoms to copy the properties of biological tissue are known in themselves. For instance, WO 98/25254 describes an artificial tissue for HF surgery, and DE 197 16 341 A1 presents a training model outfitted with artificial tissue. Patent EP 0 368 436 A2 describes a tissue phantom which copies the light-scattering properties of living tissue.

From G. C. Beck et al., Proc. SPIE 3197 (1997); G. C. Beck et al., Lasers Med. Sci. 13, 160–171 (1998); G. C. Beck, "Gewebephantomsystem und tiefenauflösender Fluoreszenznachweis für die optische Diagnostik in der Medezin," Diss. Univ. Ulm (published Dec. 21, 1998), tissue phantoms are known, which are suitable for investigating fluorescent properties of human or animal tissue. These tissue phantoms consist of a host material (for instance, polyorganic siloxane or agarose) in which the optically effective components are imbedded. These can be particles (such as Al2O3) for modeling light dispersion and coloring agents or dispersed particles (e.g., metal particles, ruby dust, or fluorescent synthetic resin particles) for modeling absorption and fluorescence. The tissue phantom material assembled in this manner is macroscopically homogeneous in arrangement or homogeneous by layer, so that on observation a largely equivalent surface impression results, including accumulated hollow spaces that simulate blood vessels.

The known tissue phantoms, however, are not appropriate for use in a device of this invention, since they either do not keep well or produce a homogeneous image upon illumination with luminescence-stimulating light. Therefore the appearance of natural tissue cannot be duplicated with sufficient exactitude, and in particular no testing or adjustment of a PDD or PDT system and no training on such a system are possible, since the degenerated tissue is not clearly distinguished from healthy tissue.

It is therefore another task of the present invention to provide a tissue phantom that is appropriate for use in a device of this invention for testing or setting a PDD or PDT system or for training on such a system, as well as the process for producing such a tissue phantom.

This task is fulfilled by the invention through the characteristics of claims 14 and 18. Because at least one additional area is present, besides the first luminescent area, and has luminescent properties which are differentiated from those of the first luminescent area, it is possible to test the recognizability of tissue alterations and thus to test or adjust a PDD or PDT system as well as to conduct training on such a system.

Here the first luminescent area, for instance, could depict a tissue alteration whereas the other area shows healthy tissue. The two areas are differentiated in their luminescent properties, for example in the intensity of the luminescence or in the wavelength range of the emitted luminescent light, so that the recognizability of the first area as opposed to the second area, for example, can be a measure of the sensitivity of the PDD system or a measure of whether the goal of user training has been met. Areas of various shapes or particular models can be used, for example similar to the model described in U.S. Pat. No. 5,820,547, with different or identical luminescent properties, in order to test the recognizability or the resolution under various conditions or to permit training under realistic conditions. Instead of a model made up of diverse areas within the tissue phantom, an arrangement of several tissue phantoms with varying properties may also be used.

In an advantageous adaptation, the tissue phantom is executed in such a way that in at least one luminescent area the luminescence fades or bleaches under the impact of illumination over time, as is observed also in the use of the PDD or PDT in vivo. The fading of the luminescence can also be a measure for the radiation dose to be set in PDT.

The fading of the luminescence, in particular, can be controlled if there is a possibility of introducing an oxygen-containing solution of a photo-sensitizer in the tissue phantom, possibly by introducing it in a hollow space in the tissue phantom. By this means the fading of the tissue phantom, or of individual parts of the tissue phantom, can be adjusted to natural conditions.

In an especially advantageous application, the tissue phantom contains at least two areas with graduated luminescent intensity, where for at least one of these areas the luminescent intensity is selected so that the recognizability of this area can allow the functionality of a PDD or PDT system to be inferred. For this purpose, the surface or spatial concentration of the luminescent material can be selected in such a way that this area can still be recognized as an altered tissue in contrast to healthy tissue. In particular, the luminescent intensity in one or several areas can be selected in such a way that it becomes possible to adjust the PDD or PDT system to a standard sensitivity or color. For example, there also can be a number of equally large areas with a luminescent intensity varying by a factor of 2 to one another. The number of areas that can still be recognized with a particular PDD or PDT system, or that are recognized by a user, can then serve as a measure for the sensitivity of the system or for the quality of the setting of the system for this user.

In the invention's process for producing a tissue phantom, a first tissue phantom material in liquid form is poured into a mold, which preferably contains several recesses separated from one another, so that a thin layer extending over these recesses links them to one another. The surface can be shaped by imposition of a plate; for example, with the help of a sandblasted plate a uniformly rough surface can be produced. After hardening and removal from the mold, the blank is turned over and laid on its upper surface, and a second tissue phantom material is poured into the existing recesses, which present a reverse image of the mold. In order to receive a tissue phantom of uniform thickness, an additional material can then be added. In this same way, additional layers can be added on to the entire tissue phantom.

This process results in a tissue phantom with uniform surface, if desired, but of non-homogeneous composition, so that with corresponding composition of the casting materials, the tissue phantom has areas with varying luminescent properties. Likewise, a tissue phantom according to this invention can be produced through the joining together of diverse, separately produced areas.

Such a tissue phantom for use in a device of this invention or a process of this invention is preferably constructed from a firm or gel-like host material, can keep for some time, and can be standardized at least with respect to its optical properties.

Tissue phantoms have proved suitable for the examination of the fluorescent properties of tissue, for instance the effect of volume-scatter and fluorescent effects on the surface appearance of the tissue at illumination with fluorescence-stimulant light, if the tissue phantoms use polyorgano siloxane as host material, aluminum particles for modeling of the light scattering and color substance, or dispersed particles for modeling absorption and luminescence (G. C. Beck et al., Proc. SPIE 3197 [1997]). The known tissue phantoms, however, are not optimal for imitating the optical properties of biological tissue.

It is therefore an additional task of the invention to produce a tissue phantom which imitates still better the optical, especially the luminescent, properties of biological and particularly human tissue.

This task is fulfilled through the characteristics of claim 20. In particular, it is preferable to use (in percent weight)
  86% silicon A and 10% silicon B, although silicon with a different composition can also be used,
  4% of a substance from the group ZnO, BaSO4, Al2O3, MgO, or similar colorless oxides as powder, in particular Al2O3 (obtainable as polishing agent with a particle size between 0.03 and 50 micrometers, where the 50% value preferably is 6 micrometers),
  0.028% to 0.036%, preferably 0.032%, of an organic or inorganic pigment, particularly Bayferrox 130 (Bayer AG, DE), and possibly 0.002% to 2%, preferably 0.2%, modified amino resin particles injected with fluorescent dye, such as Leutalux TIS flame-red (Leuchtstoffwerk Heidelberg, DE.).

This material is preferably used, without the last-named component (a non-fluorescent or slightly fluorescent initial tissue phantom material), to perform the process for producing a tissue phantom to portray healthy tissue; the material is used with the last-named component, as fluorescent second or subsequent tissue phantom material, to portray altered tissue. It can be necessary here to mix various fluorescent coloring agents together in order to copy the desired fluorescent properties of the tissue.

The invention's device and the invention's process, in which the invention's tissue phantom is preferably used, permit the simple, realistic testing of the entire PDD or PDT system. In particular, it is possible that the producer of such a system would verify the proper functioning of the system, including luminescence detection, before delivering the system to a client. At the same time the system can also be used for justifying the individual component and particularly for inspecting the adjustment of a filter system, if such be present.

Likewise it is possible, immediately before the use of a PDD or PDT system, to check the proper functioning of the system or to adapt it for a particular application. Consequently, physicians have the possibility, in the event of a negative result of a PDD examination, of convincing themselves of the impeccable condition of the PDD system being used.

The invention's device also permits the training of physicians in the use of PDD or PDT system, without burdening the patient at the same time.

The invention is more fully described hereafter with the help of two models of the invention device.

DETAILED DESCRIPTION OF THE DRAWINGS

Figure 1:
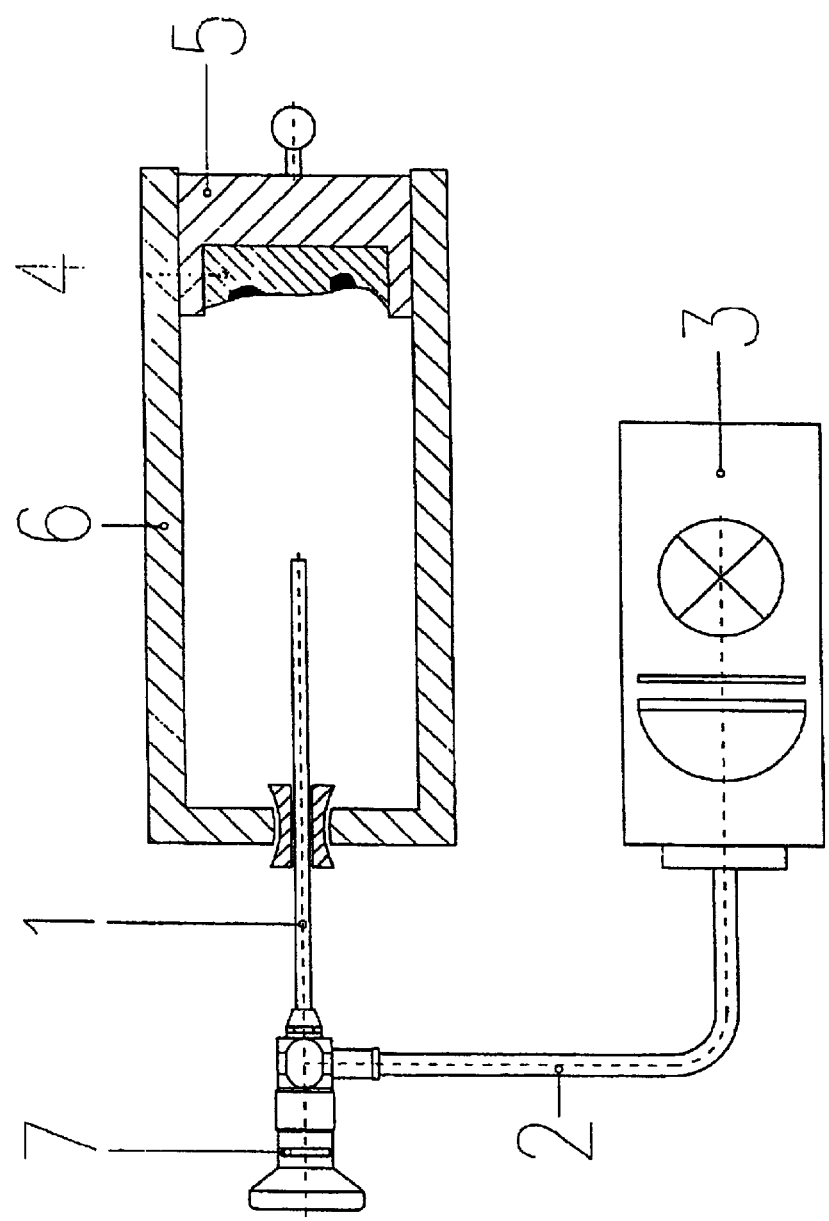
FIG. 1 shows a cross-section of a model of a device according to the invention for testing or setting PDD or PDT systems or for training on such systems.

In the model illustrated in FIG. 1, an endoscopic PDD or PDT system consists of a rigid endoscope 1, a lighting cable 2, and a PDD or PDY lighting system 3. The rigid endoscope, in known manner, includes a lens (not shown), a relay lens system, and an eyepiece for observing the image produced by the lens mounted at the distal end (in FIG. 1, to the right), which image continues the relay lens system to the proximal end (in FIG. 1, to the left). Alternatively, or in addition, to a visual observation, a video camera may be flange-mounted on the eyepiece, in a known manner. The PDD or PDT lighting system 3 features an illuminating system whose light serves to stimulate a fluorescent material and produce light for lighting the surrounding area. The lighting system 3 can include several narrow or broadband light sources for this purpose.

The invention's device in the illustrated model includes a piston 6 in which a tissue phantom 4 is mounted in replaceable manner on a carrier 5, here a sliding, definitely positionable plunger, to allow different distances to be set between the distal end of the endoscope and the tissue phantom.

The endoscope is introduced into the housing through a light-sealed closing and is secured by it at the same time.

The plunger 5 and piston 6 are designed to form a light-sealed hollow space so that the endoscope can be tested under realistic conditions or training can take place on the PDD or PDT system under working conditions.

The tissue phantom 4 contains, for example, two luminescent areas (shown in black in FIG. 1) which are mounted on the surface of a low-luminescent or non-luminescent matrix and whose shape, size, depth measure, and so on can be preset in order to imitate particular types of tissue alterations. The side of tissue phantom 4 facing the distal end of the endoscope reflects the light emerging from lighting system 3, although the reflection and volume-scattering properties are adjusted to those of the tissue to be examined. In addition, the light on impact stimulates the luminescent areas of the tissue phantom 4 to luminescence.

If necessary, an optical filter 7, with which an appropriate radiation adjustment is carried out, is situated in the proximal end of the endoscope 1 in front of the observer's eye or before the camera for adjusting the emission spectrum of the tissue phantom to the emission spectrum of the tissue.

The tissue phantom 4 can include a series of identically shaped and sized areas that contain various amounts of luminescent material; for instance, each can have twice as much concentrate as its neighboring area. Upon illumination by the luminescence-controlling light, the functionality of the PDD or PDT system can be inferred on the basis of the number of clearly recognizable luminescent areas.

If the proto-porphyrin IX (PPIX) induced through a dose of amino levulinic acid (5-ALA) is used as fluorescent coloring agent, then it is preferable for the light stimulant to lie in a wavelength range of 410 nm +/−25 nm and for the tissue phantom to radiate light in a wavelength of about 635 nm and 695 nm.

Figure 2:
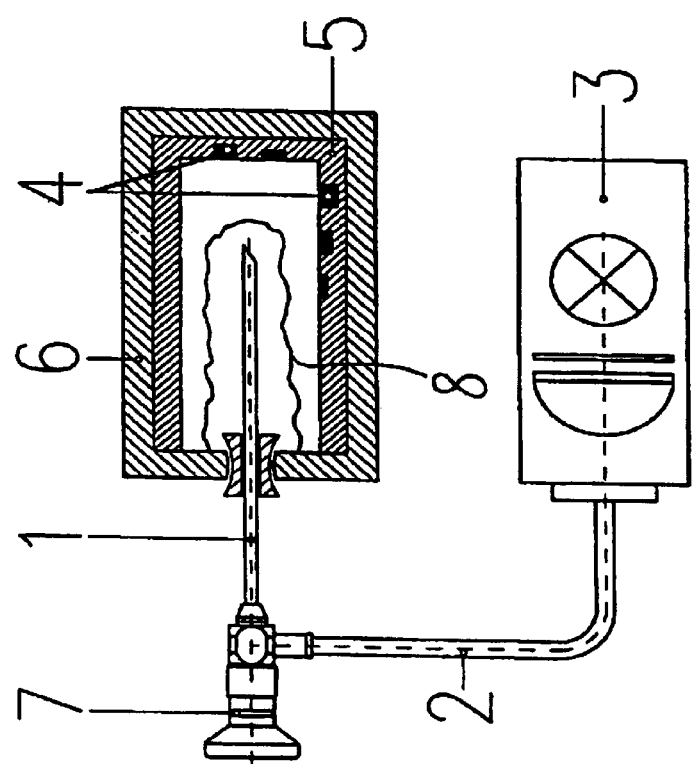
FIG. 2 shows a cross-section of an additional model of a device according to the invention.

The model illustrated in FIG. 2 corresponds to the one in FIG. 1 except that the bearer 5 of the several tissue phantoms 4 shown therein is designed so that the impression of a tube-shaped organ is copied. Also to permit the use of the invention's device in a sterile area or with sterile implements or instruments, it is also advantageous if a sterile foil 8 is placed in the housing to protect the sterile part of the implement or instrument from contamination each time it is introduced.

What is claimed is:

1. Testing, configuring, or training device for a PDD or PDT system, which includes a lighting system
   where the device is provided with a housing in which the PDD or PDT system can be at least partially accommodated, characterized in that
   a tissue phantom is accommodated in the housing in such a way that the surface of the tissue phantom can be at least partially illuminated by the lighting system and the tissue phantom has at least one luminescent area.

2. Device according to claim 1, characterized in that the housing has a hollow area in which the PDD or PDT system for testing, configuring, or training can be at least partially accommodated.

3. Device according to claim 2, characterized in that the hollow area is closed off and has at least one aperture equipped with a sealing device to accommodate part of the PDD or PDT system.

4. Device according to claim 1, characterized in that a sterile foil protects a sterile portion of the device from contamination.

5. Device according to claim 1, characterized in that the tissue phantom is secured on a movable holder.

6. Device according to claim 1, characterized in that the tissue phantom is secured in the housing in such a way that it can be exchanged.

7. Device according to claim 1, characterized in that several tissue phantoms are installed in the housing.

8. Device according to claim 1, characterized in that the tissue phantom copies the optical, thermal, electrical, or mechanical characteristics of a particular human or animal tissue or organ.

9. Device according to claim 8, characterized in that the portion of the tissue phantom that is to be illuminated by the lighting system copies colors and luminescent characteristics of a particular tissue area.

10. Device according to claim 1, characterized in that the portion of the tissue phantom that is to be illuminated by the lighting system is shaped in such a way that the surface shape of a certain tissue area is copied.

11. Device according to claim 10, characterized in that the portion of the tissue phantom that is to be illuminated by the lighting system has the shape of a hollow tube.

12. Device according to claim 1, characterized in that a filter system or additional lighting system is provided, through which the emission spectrum of the tissue phantom is adjusted in vivo to the emission spectrum of a particular bodily tissue.

13. Testing or configuring device for a PDD or PDT system, which Includes a lighting system and an observation system, characterized by the following steps:
- the PDD or PDT system to be tested or configured is at least partially accommodated in a housing or device in accordance with claim 1;
- the surface of the tissue phantom is at least partially illuminated by the lighting system;
- the illuminated surface of the tissue phantom is at least partially observed by the observation system;
- at least one measurement or one observation result is recorded, which is a measurement for the luminescent intensity or for the reporting sensitivity or functionality of the PDD or PDT system; and
- if necessary a corrective adjustment of the PDD or PDT system will be made.

14. Tissue phantom to be used in a device in accordance with claim 1, which tissue phantom includes at least a first luminescent area, characterized in that it has at least one additional area, whose luminescent properties are distinguished from those of the first luminescent area.

15. Tissue phantom according to claim 14, characterized in that in at least one luminescent area the luminescence is dimmed through the action of a lighting device.

16. Tissue phantom according to claim 15, characterized in that a means is provided for introducing an oxygen-containing solution of a photo-sensitizer into the tissue phantom.

17. Tissue phantom according to claim 14, characterized in that the tissue phantom contains at least two areas with graduated luminescent intensity, so that for at least one of these areas the luminescent intensity is selected in such a way that the recognition of this area can permit the determination of the functionality of a PDD or PDT system.

18. A device according the claim 1, wherein the tissue phantom comprises a molded cast comprising a first material having at least one depth and a second material located in the at least one depth, wherein the second material has luminescent characteristics that differ from those of the first material.

19. A device according to claim 1, wherein the tissue phantom has at least one luminescent material comprising silicon, wherein:
- between 0.5% to 10% of the luminescent material comprises a colorless oxide as powder; and
- less than 1% of the luminescent material comprises an organic or inorganic pigment,
- and less than 2% of the luminescent material comprises fluorescent particles instilled with coloring agent.

* * * * *